US012337968B2

(12) United States Patent
Edquist et al.

(10) Patent No.: US 12,337,968 B2
(45) Date of Patent: Jun. 24, 2025

(54) INTELLIGENT CENTRALIZED LAVATORY CONTROLLER ARCHITECTURE FOR TOUCHLESS LAVATORY

(71) Applicant: B/E AEROSPACE, INC., Winston Salem, NC (US)

(72) Inventors: John Edquist, Milwaukee, WI (US); Sanjay Bajekal, Simsbury, CT (US); Frank Hashberger, Snohomish, WA (US); Fangzhong Guo, Snohomish, WA (US)

(73) Assignee: B/E AEROSPACE, INC., Winston Salem, NC (US)

( * ) Notice: Subject to any disclaimer, the term of this patent is extended or adjusted under 35 U.S.C. 154(b) by 172 days.

(21) Appl. No.: 17/209,715

(22) Filed: Mar. 23, 2021

(65) Prior Publication Data

US 2022/0306296 A1    Sep. 29, 2022

(51) Int. Cl.
*B64D 11/02*   (2006.01)
*A61L 2/10*    (2006.01)
*A61L 2/24*    (2006.01)

(52) U.S. Cl.
CPC ............ *B64D 11/02* (2013.01); *A61L 2/10* (2013.01); *A61L 2/24* (2013.01); *A61L 2202/14* (2013.01)

(58) Field of Classification Search
CPC .................................................. B64D 11/02
See application file for complete search history.

(56) References Cited

U.S. PATENT DOCUMENTS

| 9,477,317 | B1 | 10/2016 | Clements |
| 9,802,561 | B2 | 10/2017 | Scheffler et al. |
| 10,130,727 | B1 | 11/2018 | Byrnes et al. |
| 10,301,806 | B2 | 5/2019 | Childress et al. |
| 10,668,178 | B2 | 6/2020 | Brockschmidt |
| 10,702,618 | B2 | 7/2020 | Callahan |
| 2007/0231193 | A1* | 10/2007 | Jung ............... A61L 2/084 250/455.11 |
| 2008/0131332 | A1* | 6/2008 | Nguyen ............ A61L 2/24 422/119 |

(Continued)

FOREIGN PATENT DOCUMENTS

| CN | 112153991 | * 12/2020 | ............... A61L 2/10 |
| EP | 3287146 | 2/2018 | |
| WO | 2019190967 | 10/2019 | |

OTHER PUBLICATIONS

European Patent Office; European Search Report dated Jul. 27, 2022 in Application No. 22163831.5.

(Continued)

*Primary Examiner* — Huyen D Le
(74) *Attorney, Agent, or Firm* — SNELL & WILMER L.L.P.

(57) ABSTRACT

A system for touchless control of a lavatory of an aircraft includes at least one sensor located in the lavatory and configured to detect detected data corresponding to the lavatory. The system further includes at least one actuator or light source located in the lavatory and configured to perform an action. The system further includes a central controller coupled to the at least one sensor and the at least one actuator or light source and configured to make an inference based on the detected data and to control the at least one actuator or light source based on the inference.

18 Claims, 8 Drawing Sheets

(56) References Cited

U.S. PATENT DOCUMENTS

| | | | |
|---|---|---|---|
| 2012/0186654 A1 | 7/2012 | Dannenberg et al. | |
| 2016/0220716 A1 | 8/2016 | Childress et al. | |
| 2017/0049915 A1 | 2/2017 | Brais et al. | |
| 2017/0246331 A1 | 8/2017 | Lloyd | |
| 2017/0290935 A1 | 10/2017 | Boodaghians et al. | |
| 2018/0055959 A1 | 3/2018 | Lin et al. | |
| 2018/0064833 A1 | 3/2018 | Childress et al. | |
| 2018/0369434 A1* | 12/2018 | Callahan | A61L 2/26 |
| 2018/0369440 A1 | 12/2018 | Dytioco et al. | |
| 2018/0371733 A1 | 12/2018 | Childress | |
| 2019/0030195 A1 | 1/2019 | Hatti et al. | |
| 2019/0078308 A1 | 3/2019 | McIntosh | |
| 2019/0087788 A1 | 3/2019 | Murphy et al. | |
| 2019/0290795 A1 | 9/2019 | Brockshmidt | |
| 2020/0164988 A1* | 5/2020 | Alvarez | B64D 45/00 |
| 2020/0331611 A1 | 10/2020 | Hack et al. | |
| 2022/0111087 A1* | 4/2022 | Childress | A61L 2/24 |

OTHER PUBLICATIONS

European Patent Office; European Search Report dated Jul. 27, 2022 in Application No. 22163846.3.

USPTO; Requirement for Restriction dated May 22, 2023 in U.S. Appl. No. 17/209,684.

USPTO; Non-Final Office Action dated Jul. 26, 2023 in U.S. Appl. No. 17/209,684.

USPTO; Final Office Action dated Dec. 11, 2023 in U.S. Appl. No. 17/209,684.

European Patent Office, European Office Action dated Feb. 26, 2024 in Application No. 22163831.5.

European Patent Office, European Office Action dated Feb. 22, 2024 in Application No. 22163846.3.

USPTO; Non-Final Office Action dated Mar. 5, 2024 in U.S. Appl. No. 17/209,684.

USPTO; Final Office Action dated Jun. 20, 2024 in U.S. Appl. No. 17/209,684.

* cited by examiner

INTELLIGENT CENTRALIZED LAVATORY CONTROLLER ARCHITECTURE FOR TOUCHLESS LAVATORY

FIELD

The present disclosure relates to systems and methods for control of features of an aircraft lavatory by a central controller.

BACKGROUND

Conventional aircraft lavatories include numerous electronic functions such as a toilet flush, sink water flowing, lighting, and signage that each have individual controllers and power sources. This results in circuit breaker sizing and wiring to each function to be oversized in order to compensate for worst-case scenarios in which each function is operating simultaneously. When an aircraft operator desires to add additional functions (such as a new light source), the addition may result in significant rewiring of the lavatory, extra weight added to the aircraft, and extra power draw because a new controller will also be installed.

It is therefore desirable to develop systems and methods that reduce weight and power draw of aircraft lavatories and facilitate addition of new functions with relative ease.

SUMMARY

Disclosed herein is a system for touchless control of a lavatory of an aircraft. The system includes at least one sensor located in the lavatory and configured to detect detected data corresponding to the lavatory. The system further includes at least one actuator or light source located in the lavatory and configured to perform an action. The system further includes a central controller coupled to the at least one sensor and the at least one actuator or light source and configured to make an inference based on the detected data and to control the at least one actuator or light source based on the inference.

In any of the foregoing embodiments, the at least one sensor includes a touchless sensor configured to receive user input corresponding to requested operation of a component of the lavatory, and the central controller is further configured to control the at least one actuator or light source based on the user input.

In any of the foregoing embodiments, the at least one sensor includes: a touchless seat sensor configured to receive a toilet seat request corresponding to a request to lift a toilet seat of the lavatory; a touchless lid sensor configured to receive a toilet lid request corresponding to a request to lift a toilet lid of the lavatory; a touchless soap sensor configured to receive a soap dispense request corresponding to a request to dispense soap within the lavatory; a touchless faucet sensor configured to detect a faucet request corresponding to a request to operate a faucet of the lavatory; a touchless flush sensor configured to detect a flush request corresponding to a request to flush a toilet of the lavatory; and a touchless trash sensor configured to detect a trash flap request corresponding to a request to actuate a trash flap of the lavatory.

Any of the foregoing embodiments may further include an actuator controller coupled to the at least one actuator or light source and the central controller, wherein the central controller is configured to control the at least one actuator or light source by transmitting a control request to the actuator controller.

In any of the foregoing embodiments, the at least one actuator or light source includes an ultraviolet light source located in the lavatory and configured to emit ultraviolet light having a wavelength that at least one of injures, neutralizes, or kills pathogens, and wherein the central controller is further coupled to the ultraviolet light source and configured to control the ultraviolet light source based on the detected data.

In any of the foregoing embodiments, the at least one actuator or light source further includes a visible light source located in the lavatory and configured to emit visible light having a visible wavelength, wherein the central controller is further configured to control the at least one actuator or light source to cause a total power draw of the system to remain at or below a power threshold corresponding to a maximum amount of power available to the system.

In any of the foregoing embodiments, the central controller is further configured to control the at least one actuator or light source to at least partially operate sequentially to cause the total power draw of the system to remain at or below the power threshold.

In any of the foregoing embodiments, the central controller is further configured to determine a health status of the system including at least one of a remaining life of the ultraviolet light source, surface wear experienced by surfaces of the lavatory in response to the ultraviolet light, or a remaining quantity of supplies in the lavatory, and to control at least one of the at least one actuator or light source further based on the health status.

In any of the foregoing embodiments, the inference includes at least one of an inferred portion of the lavatory used by a passenger for which sanitization is desirable or whether the lavatory is occupied.

Also disclosed is a system for touchless control of a lavatory of an aircraft. The system includes multiple sensors located in the lavatory and configured to detect detected data corresponding to the lavatory. The system further includes multiple actuators or light sources located in the lavatory and each configured to perform an action. The system further includes a central controller coupled to each of the multiple sensors and each of the multiple actuators or light sources and configured to make an inference based on the detected data and to control the multiple actuators or light sources based on the inference.

In any of the foregoing embodiments, the multiple sensors include: a touchless seat sensor configured to receive a toilet seat request corresponding to a request to lift a toilet seat of the lavatory, a touchless lid sensor configured to receive a toilet lid request corresponding to a request to lift a toilet lid of the lavatory; a touchless soap sensor configured to receive a soap dispense request corresponding to a request to dispense soap within the lavatory, a touchless faucet sensor configured to detect a faucet request corresponding to a request to operate a faucet of the lavatory, a touchless flush sensor configured to detect a flush request corresponding to a request to flush a toilet of the lavatory, and a touchless trash sensor configured to detect a trash flap request corresponding to a request to actuate a trash flap of the lavatory; and the multiple actuators or light sources include: a toilet seat actuator configured to actuate the toilet seat, a soap actuator configured to dispense the soap, a faucet actuator configured to actuate the faucet, a trash flap actuator configured to actuate the trash flap, a visible light source configured to emit visible light; and an ultraviolet light source configured to emit ultraviolet light having a wavelength that at least one of injures, neutralizes, or kills pathogens.

In any of the foregoing embodiments, the central controller is further configured to control each of the multiple actuators or light sources to cause a total power draw of the system to remain at or below a power threshold corresponding to a maximum amount of power available to the system.

In any of the foregoing embodiments, the central controller is further configured to determine a health status of the system including at least one of a remaining life of the ultraviolet light source, surface wear experienced by surfaces of the lavatory in response to the ultraviolet light, or a remaining quantity of supplies in the lavatory, and to control at least one of the multiple actuators or light sources further based on the health status.

In any of the foregoing embodiments, the inference includes at least one of an inferred portion of the lavatory used by a passenger for which sanitization is desirable or whether the lavatory is occupied.

Also disclosed is a method for touchless control of a lavatory of an aircraft. The method includes detecting, by at least one sensor of the lavatory, detected data corresponding to the lavatory. The method further includes making, by a central controller, an inference based on the detected data. The method further includes controlling, by the central controller, at least one actuator or light source of the lavatory based on the inference.

In any of the foregoing embodiments, the at least one sensor includes multiple sensors, and wherein the at least one actuator or light source includes at least one actuator and at least one light source.

In any of the foregoing embodiments, the central controller is further configured to control the at least one actuator and the at least one light source to cause a total power draw of the lavatory to remain at or below a power threshold corresponding to a maximum amount of power available to the lavatory.

In any of the foregoing embodiments, the central controller is further configured to control the at least one actuator and the at least one light source to operate sequentially to cause the total power draw of the system to remain at or below the power threshold.

Any of the foregoing embodiments may further include determining, by the central controller, a health status of the system including at least one of a remaining life of the at least one light source, surface wear experienced by surfaces of the lavatory in response to light emitted by the at least one light source, or a remaining quantity of supplies in the lavatory, wherein controlling the at least one actuator or light source includes controlling the at least one actuator or light source further based on the health status.

In any of the foregoing embodiments, the inference includes at least one of an inferred portion of the lavatory used by a passenger for which sanitization is desirable or whether the lavatory is occupied.

The foregoing features and elements may be combined in various combinations without exclusivity, unless expressly indicated otherwise. These features and elements as well as the operation thereof will become more apparent in light of the following description and the accompanying drawings. It should be understood, however, the following description and drawings are intended to be exemplary in nature and non-limiting.

BRIEF DESCRIPTION OF THE DRAWINGS

The subject matter of the present disclosure is particularly pointed out and distinctly claimed in the concluding portion of the specification. A more complete understanding of the present disclosure, however, may best be obtained by referring to the detailed description and claims when considered in connection with the figures, wherein like numerals denote like elements.

DETAILED DESCRIPTION

The detailed description of exemplary embodiments herein makes reference to the accompanying drawings, which show exemplary embodiments by way of illustration. While these exemplary embodiments are described in sufficient detail to enable those skilled in the art to practice the exemplary embodiments of the disclosure, it should be understood that other embodiments may be realized and that logical changes and adaptations in design and construction may be made in accordance with this disclosure and the teachings herein. Thus, the detailed description herein is presented for purposes of illustration only and not limitation. The steps recited in any of the method or process descriptions may be executed in any order and are not necessarily limited to the order presented.

Furthermore, any reference to singular includes plural embodiments, and any reference to more than one component or step may include a singular embodiment or step. Also, any reference to attached, fixed, connected or the like may include permanent, removable, temporary, partial, full and/or any other possible attachment option. Additionally, any reference to without contact (or similar phrases) may also include reduced contact or minimal contact. Surface shading lines may be used throughout the figures to denote different parts but not necessarily to denote the same or different materials.

The present disclosure is directed to a centralized intelligent controller for controlling various features of an aircraft lavatory. The controller may communicate with all lavatory functions to manage total power load and coordinate sequential behaviors within the lavatory. By connecting each piece of lavatory operation to the controller, the system is capable of prioritizing functions, creating automated sequences, and reducing an overall system size, weight, and complexity.

The systems and methods of the present disclosure provide various benefits and advantages over conventional systems and methods. An exemplary system may control various operations within the lavatory based on contextual awareness. For example, the system may close a toilet seat lid prior to flushing the toilet. As another example, the system may disinfect the lavatory using ultraviolet (UV) light in response to a sequence of a toilet flush, a sink usage, and unlatching of the lavatory door.

The system may further provide power management benefits and advantages. For example, the system may operate various functions within the lavatory sequentially or may prioritize functions in order to monitor total power usage by the system in order to remain below a threshold power budget. This is advantageous because power may originate from a single source and may be shared across all features of the lavatory.

The system further advantageously facilitates expansion and reconfiguration with relative ease. The specific system architecture enables multiple variances of touchless features and expansion without rewiring or other modifications to the system. Additionally, the system advantageously sizes motor controllers that are coupled to the motors that they power, but at least a portion of processing is performed at the central controller. This reduces complexity of the system and reduces wasted computational ability.

Additionally, a central memory may store airline-specific lighting scenes and other variable settings such as a faucet-on-time, a UV disinfectant dosage, or the like. Additionally, each central controller may control features of a single lavatory, and each central controller may be coupled together. This advantageously enables health monitoring, lavatory queueing, and total power management of the lavatories by the central controller, as well as other potential features.

Figure 1:
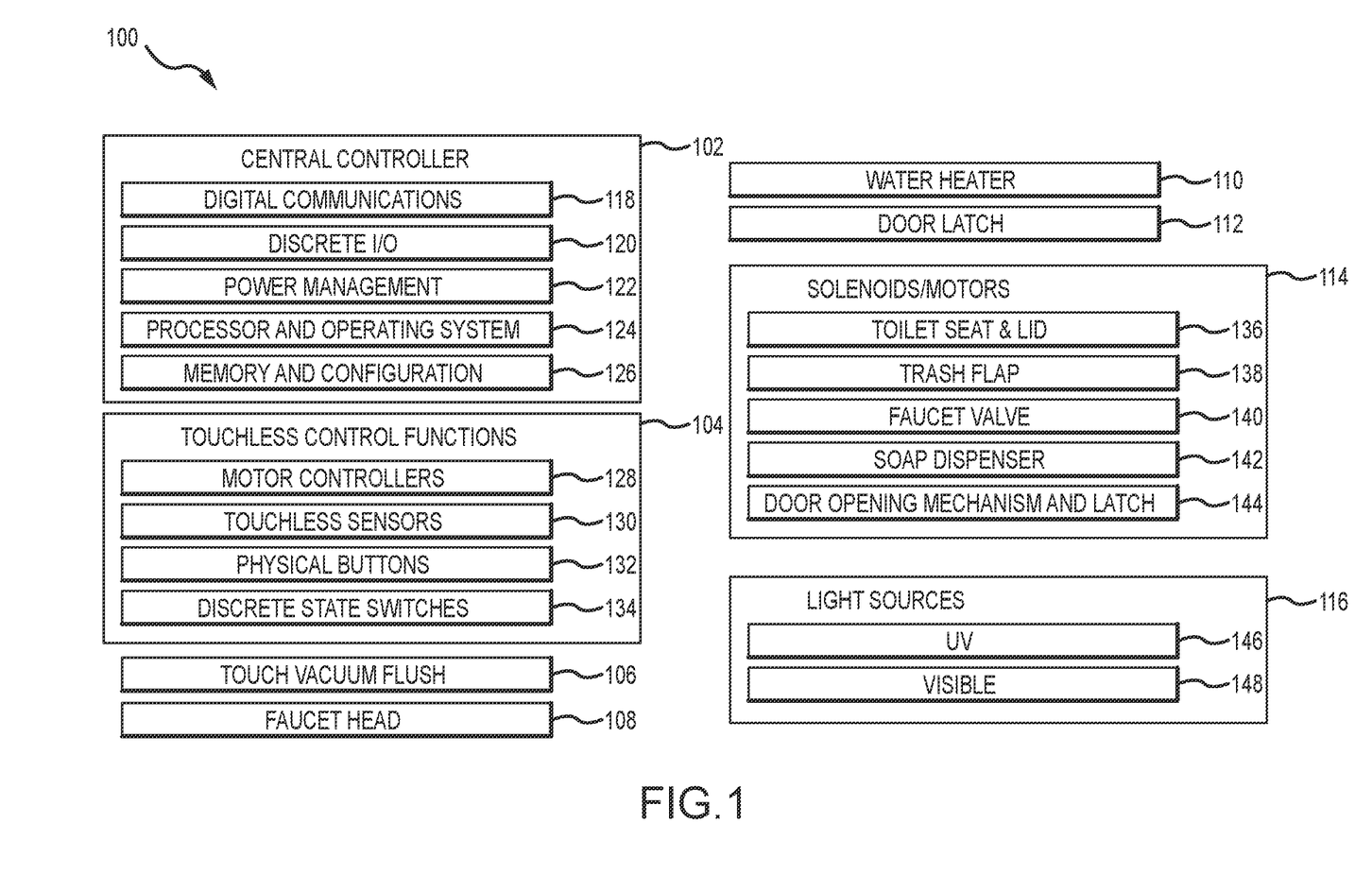
FIG. 1 illustrates a system for control of various features of an aircraft lavatory by a central controller, in accordance with various embodiments.
Figure 2:
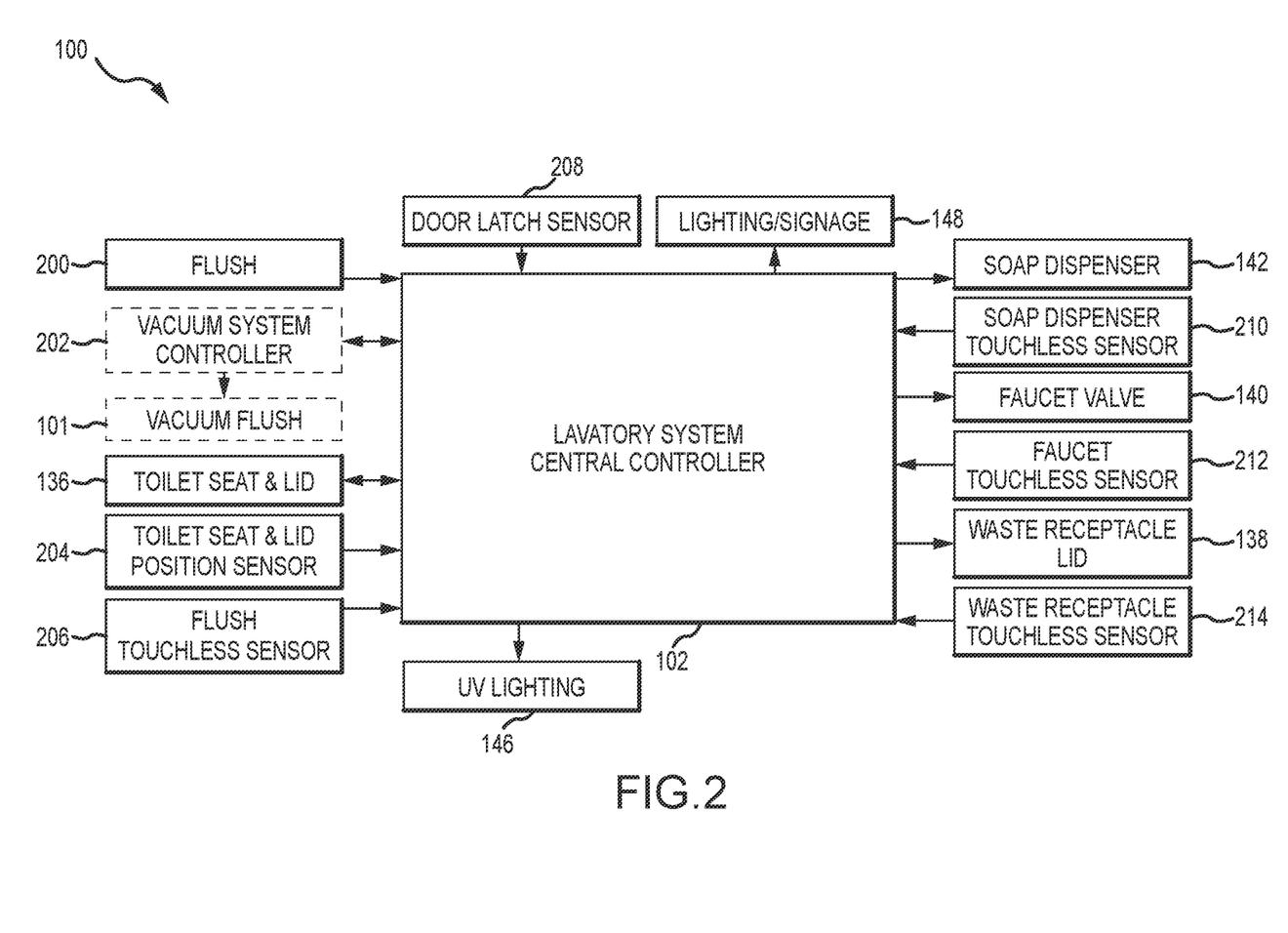
FIG. 2 illustrates additional details of the system of FIG. 1, in accordance with various embodiments.
Figure 3:
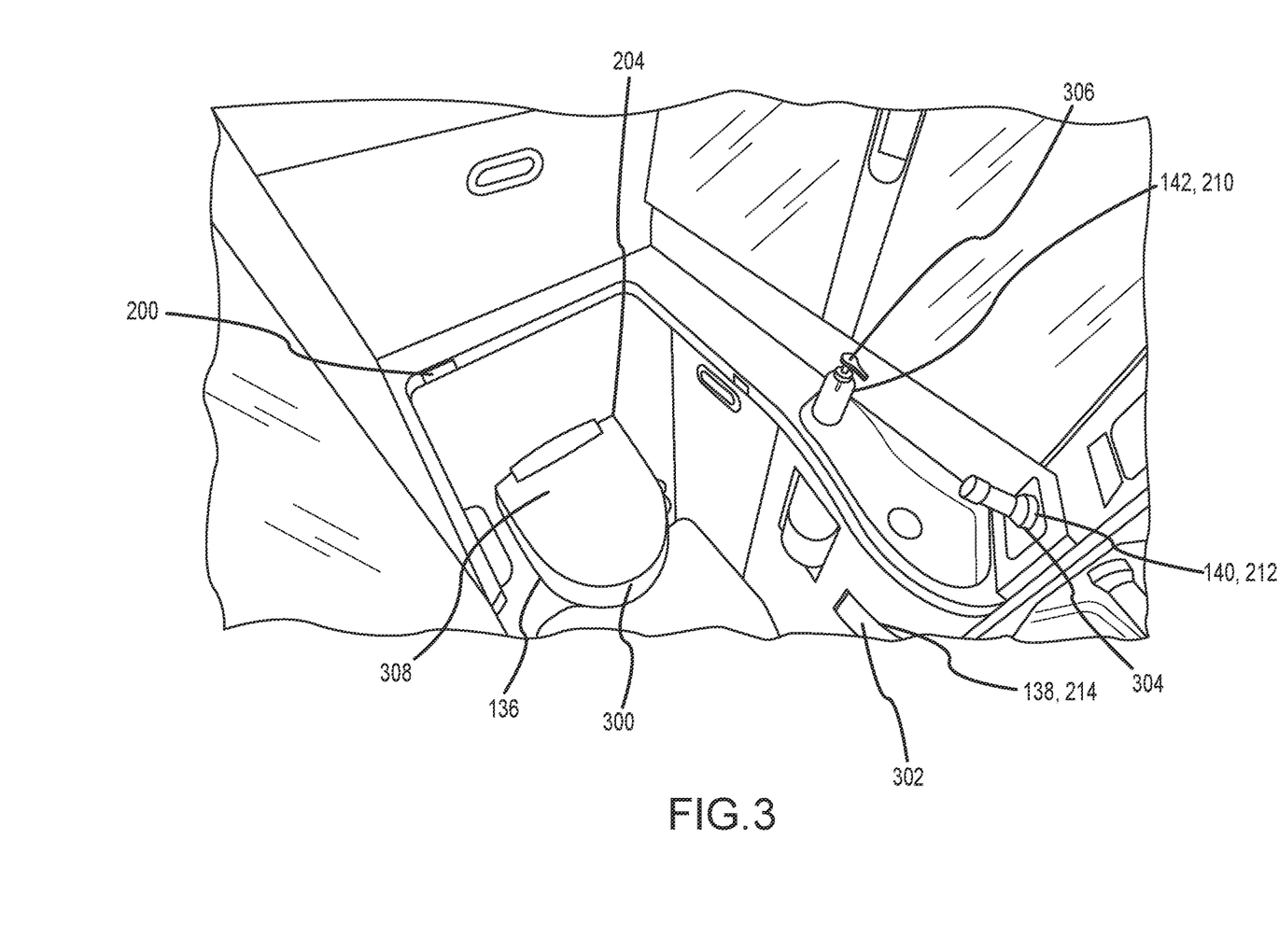
FIG. 3 illustrates additional details of the system of FIG. 1, in accordance with various embodiments.

Referring generally to FIGS. 1, 2, and 3, an exemplary system 100 includes multiple sensors, multiple actuators (which may include additional features such as a vacuum flush motor, a water heater, or the like), multiple light sources, and a central controller 102. The system 100 may further include touchless control functions 104, a toilet vacuum flush 106, a faucet head 108, a water heater 110, a door latch 112, multiple solenoids or motors 114, and multiple light sources 116.

The central controller 102 may be coupled to each feature of the system 100 and may include various units or modules capable of performing various functions. In particular, the central controller 102 may include a digital communications function 118 capable of communicating with various features of the system 100. The central controller 102 may further have an input/output function 120 capable of managing inputs and outputs of the central controller 102. The central controller 102 may further include a power management function 122 capable of monitoring and controlling power management of the system 100. The central controller 102 may further include one or more processor or controller and a corresponding operating system 124. The processor or controller may include a logic device such as one or more of a central processing unit (CPU), an accelerated processing unit (APU), a digital signal processor (DSP), a field programmable gate array (FPGA), an application specific integrated circuit (ASIC), or any other device capable of implementing logic. In various embodiments, the processor or controller may further include any non-transitory memory known in the art. The memory may store instructions usable by the logic device to perform operations as described herein. The central controller 102 may also include a memory 126 which may store airline-specific preferences and operations (such as a desirable lighting configuration or desirable ultraviolet emission time) or other information.

The touchless control functions 104 may include various features (e.g., input devices such as motion sensors or buttons) to facilitate touchless or other control of functions of the system 100. For example, the central controller 102 may control various operations within the lavatory based on information received from the touchless control functions 104. In particular, the touchless control functions may include motor controllers 128 that are each coupled to one or more solenoid, motor, or actuator of the system 100. For example, each solenoid, motor, or actuator may include a specific motor controller 128 which controls operation of the specific solenoid, motor, or actuator based on signals received from the central controller 102. The touchless control functions 104 may further include a plurality of touchless sensors 130. The touchless sensors 130 may include sensors capable of receiving user input such as a proximity sensor, a motion sensor, or the like. The user input detected by the touchless sensors 130 may correspond to a request for operation of one or more component of the system 100 (e.g., a toilet flush request). The touchless control functions 104 may further include physical buttons 132 which are likewise capable of receiving user input corresponding to a request for operation of one or more component of the system 100. The touchless control functions 104 may also include discrete state switches 134. The discrete state switches 134 may include any type of discrete switch such as a limit switch (which turn on or off in response to contact with a part or element), a reed switch (featuring a mechanical switch dependent on a position of a magnet), a proximity switch (which operate on the principles of induction), photoelectric sensors (for example, usable in part detection or material handling), or the like. The discrete state switches 134 may cause various motors or actuators to remain in a desired state.

The toilet vacuum flush 106 may include an actuator, motor, or other device or component which initiates a vacuum flush of a toilet within the laboratory. The toilet vacuum flush 106 may be controlled to initiate or cease a flush operation based on instructions received or determined by the central controller 102.

The faucet head 108 may include a sink faucet through which water may flow. A valve (faucet valve, or sink valve, 140) may be located upstream from the sink faucet and may be controlled by the central controller 102 to adjust an amount of water flowing through the faucet head 108.

The water heater 110 may include a tank or tankless water heater capable of warming water that is used in the lavatory (e.g., water flowing through the faucet head 108). The central controller 102 may control operation of the water heater 110 based on various elements of information such as information received from the touchless control functions 104, a power status of the system 100, or the like.

The door latch 112 may be used to lock or unlock a door leading into the lavatory. The door latch 112 may be automatically controlled by the central controller 102, may be manually controlled by a user (e.g., by flipping a manual switch), or the like. The door latch 112 may include a sensor that transmits information to the central controller 102 indicating whether the door latch 112 is in a locked or unlocked state.

The solenoids or motors 114 (which may also be referred to as actuators) may include various solenoids or motors capable of actuating or controlling operation of functions of the system 100. In addition, the touchless control functions 104 may include touchless or touch-activated sensors that detect a request to actuate the motor or solenoid 114 or detect other data corresponding to the system 100. In particular, the solenoids or motors 114 may include one or more toilet seat and lid motor, or actuator, 136. The toilet seat and lid motor 136 may control each of a toilet seat and a toilet lid 300 to actuate between a raised position and a lowered position. In particular the motor 136 may control the toilet seat and lid 300 to both be raised, both be lowered, or the lid raised and the seat lowered. The system 100 may further include a toilet seat and lid position sensor 204 that detects data corresponding to a state of the toilet seat and lid 300 (i.e., raised, lowered, or raised and lowered). In various embodiments, the toilet seat and lid position sensor 204 may also or instead include a touchless seat sensor capable of receiving user input corresponding to a request to lower or raise at least one of the toilet seat or the toilet lid. In that regard, the toilet seat and lid position sensor 204 may also or instead include a touchless seat sensor capable of receiving user input corresponding to a request to lower or raise the toilet seat, and a touchless lid sensor capable of receiving user input corresponding to a request to lower or raise the lid of the toilet.

The solenoids and motors 114 may also include a trash flap motor, or actuator, 138. The trash flap motor 138 may control a trash flap 302 to alternate between an open position and a closed position. The system 100 may further include a touchless trash sensor, or waste receptacle touchless sensor, 214. The trash sensor 214 may detect a request for the trash flap 302 to be opened. For example, a user may waive a hand in front of the trash sensor 214 to cause the trash flap 302 to open.

The solenoids and motors 114 may further include a faucet valve 140, or faucet actuator, 140 coupled to a faucet 304. The faucet valve 140 may open to allow water to flow through the faucet 304 and may close to reduce the likelihood of water flowing through the faucet 304. The system 100 may further include a touchless faucet sensor 212 capable of receiving user input corresponding to a request to at least one of open or close the faucet valve 140.

The solenoids and motors 114 may also include a soap dispenser, or soap actuator, 142. The soap dispenser 142 may be capable of pumping soap through an outlet or nozzle 306. The system 100 may also include a touchless soap sensor 210 capable of receiving user input corresponding to a request for soap to be dispensed from the outlet or nozzle 306.

The solenoids and motors 114 may further include a door opening mechanism and latch 144. The door opening mechanism and latch 144 may include a motor, actuator, or the like capable of opening a door to the lavatory and closing the door to the lavatory. The door opening mechanism and latch 144 may further include a latch capable of locking the lavatory door in a locked position and unlocking the lavatory door. The central controller 102 may receive information from the door opening mechanism and latch 144 indicating at least one of a current state or a previous state of the door opening mechanism and latch 144.

The system 100 may further include a flush button 200 capable of receiving user input corresponding to a request to flush a toilet 308 (e.g., via depression of the flush button 200). The system 100 may also include a touchless flush sensor 206 capable of receiving user input corresponding to a request to flush the toilet 308 (e.g., by waving a hand in front of the touchless flush sensor 206). The system 100 may further include a vacuum system controller 202 coupled to the vacuum flush 106. The vacuum system controller 202 may control the vacuum flush 106 to flush the toilet 308 based on user input received by at least one of the flush button 200 or the touchless flush sensor 206.

The light sources 116 may include one or more UV light source 146 and one or more visible light source 148. The UV light source 146 may include a light source that generates ultraviolet light having a wavelength that at least one of injures, neutralizes, or kills pathogens. The UV light source 146 may include multiple UV light sources that are each directed to a separate portion of the lavatory. For example, a first UV light source may be directed towards the toilet 308 and a second UV light source may be directed towards the faucet 304.

The visible light source 148 may include a first one or more visible light source that directs light into the lavatory to illuminate the lavatory for ease of use of a user. The visible light source 148 may further include signs indicating a current status of the lavatory (e.g., occupied or vacant).

The central controller 102 may receive information from each component of the system 100 (i.e., a status of one or more of the solenoids and motors 114, user input or other information detected or received by the touchless control functions 104, a status of one or more of the light sources 116 or other system components, or the like). The central controller 102 is further capable of making an inference based on the detected or received data, and of controlling various elements of the system 100 based on the inference. The central controller 102 is further capable of managing power drawn by each component of the system 100 and controlling the components to cause a total power draw to be less than or equal to a threshold power level that corresponds to a maximum amount of power that is available to the system 100. The central controller 102 is also capable of monitoring a health status of various components of the system (i.e., remaining lives, an amount of wear and tear experienced by surfaces as a result of the UV light sources 146, a remaining quantity of supplies such as soap or water) or the like, and to take an action based on the health status.

Figure 4:
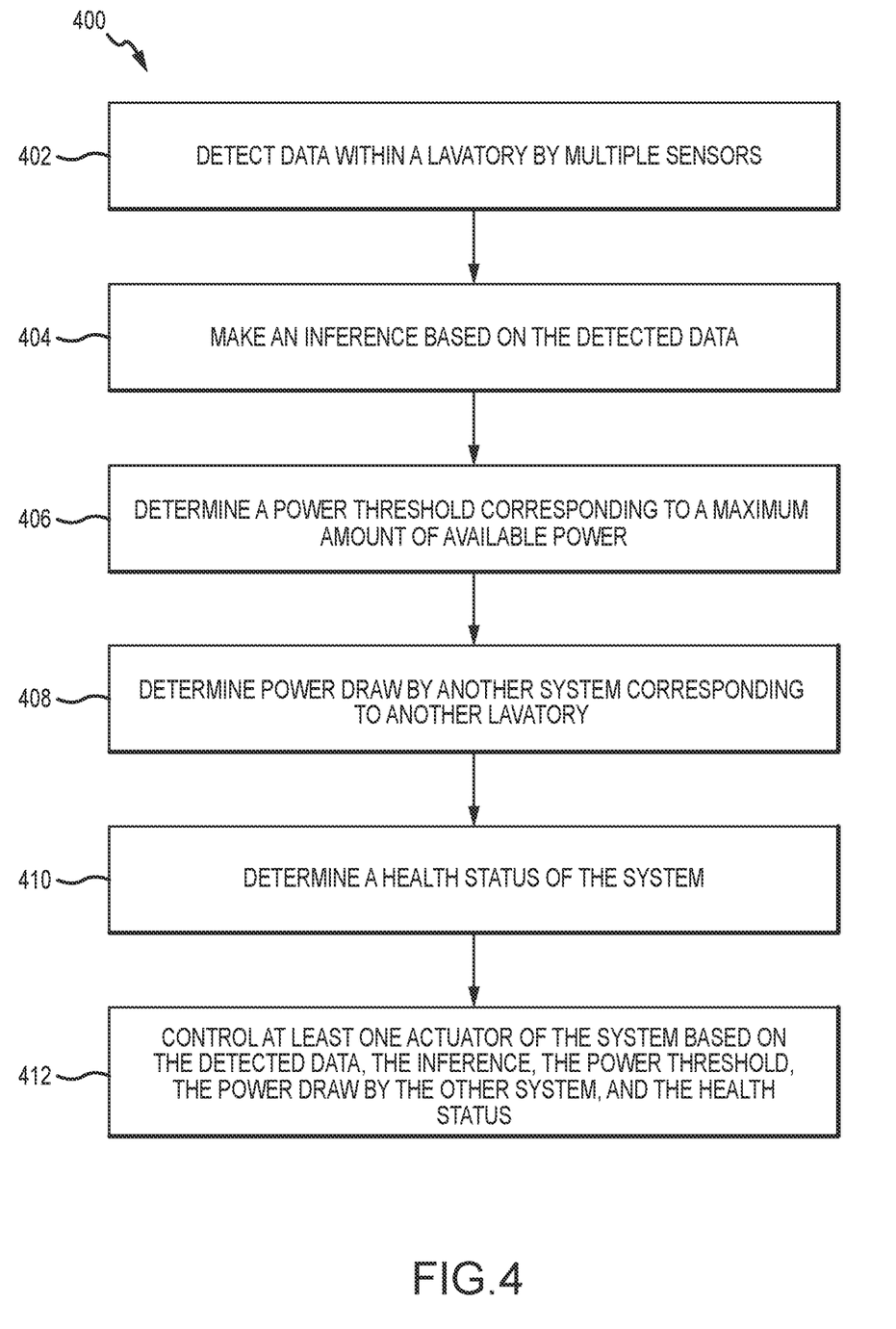
FIG. 4 illustrates a method for control of various features of an aircraft lavatory by a central controller, in accordance with various embodiments.

Referring now to FIG. 4, a method 400 for touchless control of aircraft lavatory features by a system similar to the system 100 of FIG. 1 is shown. In block 402, one or more sensor of the lavatory may detect data corresponding to the lavatory. For example, the sensor may determine whether the lavatory is occupied, a current status of one or more component of the lavatory (such as a toilet seat, a door, or a latch), whether one or more light source is generating light, a quantity of remaining supplies, or the like. The sensor may also detect user input corresponding to a request for operation of one or more feature of the lavatory such as a flush request, a request to dispense soap or water, a request to raise or lower a toilet seat or toilet lid, a request to open or close a trash flap, or the like. The detected data may be transmitted to a central controller of the system.

In block 404, the central controller may make an inference based on the detected data. For example, the inference may include an inferred portion of the lavatory that was used by the user and may be made based on, for example, whether the toilet seat or toilet lid was moved, whether soap or water was dispensed, or the like. As another example, the inference may include whether the lavatory is currently occupied. As yet another example, the inference may include whether a line to use the lavatory is forming.

In block 406, the central controller may determine a power threshold that corresponds to a maximum amount of power that is available to the lavatory. The central controller may determine the power threshold by accessing a memory (i.e., the memory may be programmed with the power threshold), may receive the power threshold from an operator of the aircraft, may calculate the power threshold based on a received power signal, or the like.

In block 408, the central controller may determine a current amount of power drawn by another system that corresponds to another lavatory on the aircraft. For example, the central controller may make this determination based on information received from various components of the other lavatory or from a signal received by a central controller that is responsible for the other lavatory.

In block 410, the central controller may determine a health status of the system. The central controller may, for example, determine the health status based on the data that was detected in block 402. For example, a sensor located within a soap dispenser may detect a remaining quantity of soap within the soap dispenser. As yet another example, a sensor located within a toilet paper hold may detect a remaining quantity of toilet paper within the toilet paper hold. The central controller may, for example, determine the health status based on a duration of use of various components of the system. For example, the central controller may record a duration of each use of an ultraviolet light and a duration for which one or more surface was exposed to the ultraviolet light. The central controller may be programmed to know that certain surfaces degrade to or past a threshold in response to a first duration of exposure of ultraviolet light. The central controller may determine the health status of the various surfaces based on the duration of each use, the one or more exposed surfaces, and the threshold duration. The central controller may, for example, determine the health status based on an operation of one or more motor or actuator. For example, if a motor is instructed to rotate at 25 revolutions per minute (RPM) and is only rotating at 10 RPM, the central controller may determine that the motor may require service.

In block 412, the central controller may control at least one actuator of the system based on at least one of the detected data from block 402, the one or more inference from block 404, the power threshold from block 406, the power draw by the other system from block 408, or the health status from block 410.

FIGS. 5 through 8 illustrate various exemplary uses of the method 400 by the system 100 of FIG. 1. Referring to FIGS. 1 and 5 through 8, only certain features of the system 100 are shown and discussed in the examples. In particular, the examples discuss the central controller 102 which is coupled to each of the touchless flush sensor 206, the vacuum flush 106, the sink valve 140, the UV light source 146, general visible light sources for illuminating the lavatory 148A, light sources for illuminating signs 148B, the door latch 112, and a health monitoring function 500 (which may be implemented in the central controller 102 or in another location).

Figure 5:
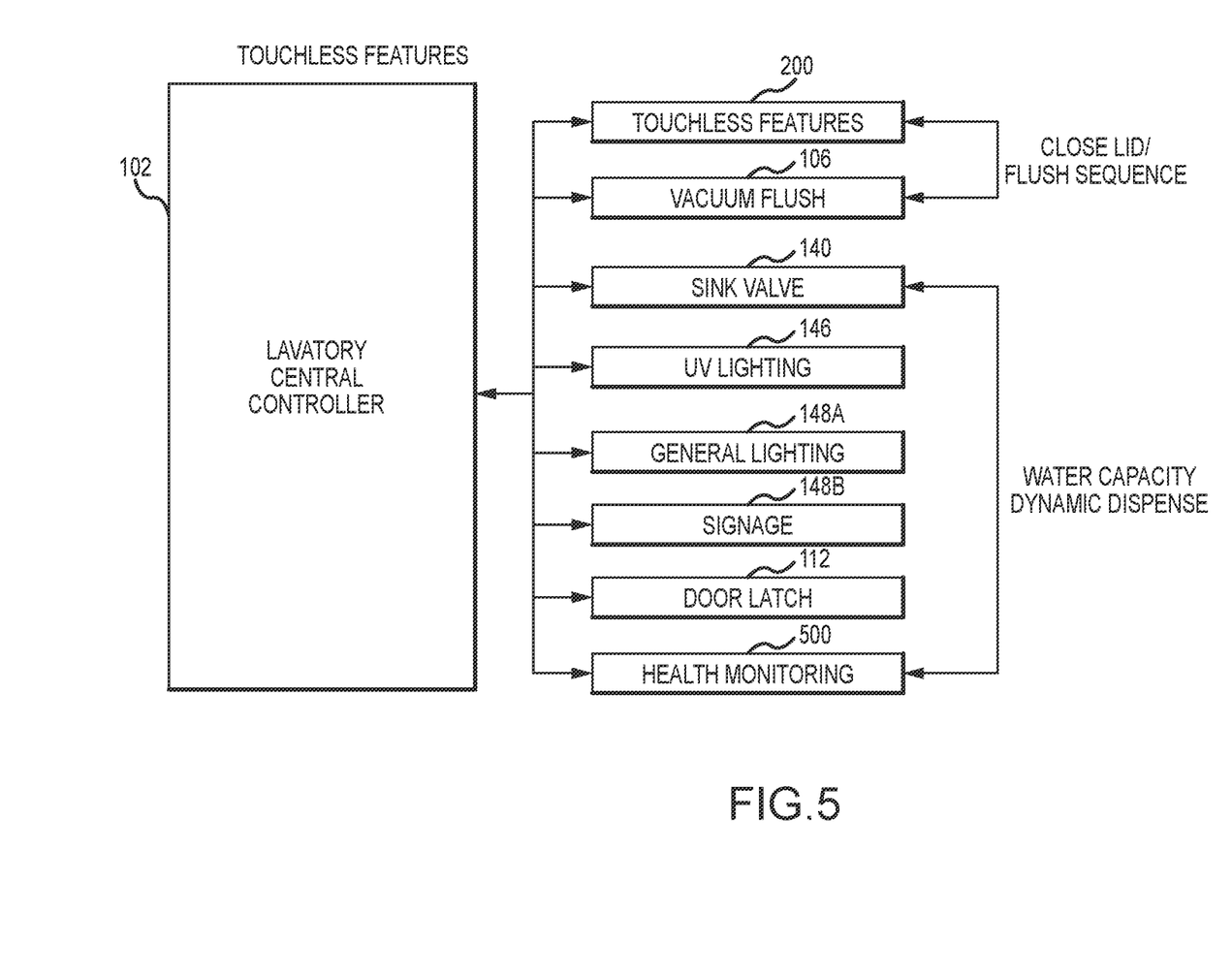
FIGS. 5, 6, 7, and 8 illustrate exemplary implementations of the method of FIG. 4 by the system of FIG. 1, in accordance with various embodiments.

Referring to FIGS. 4 and 5, an exemplary use of the method 400 for touchless control of the lavatory is shown. In particular, the touchless flush sensor 206 may receive user input corresponding to a request to flush the toilet. The central controller 102 may control the vacuum flush 106 to flush the toilet in response to the touchless flush sensor 206 receiving the user input. Continuing the example, the central controller 102 may control the vacuum flush 106 based on information other than the touchless flush sensor 206. For example, the central controller 102 may determine to activate the vacuum flush 106 after the toilet lid has been opened and then closed, indicating that a user has used the toilet and then completed the use of the toilet.

The health monitoring 500 may further monitor a quantity of water within a reservoir. In response to a user requesting opening of the sink valve 140, the central controller 102 may open the sink valve 140 for a first amount of time. In response to the reservoir reaching or dropping below a threshold water level, the central controller 102 may reduce the amount of time which the sink valve 140 is open in order to conserve water.

Figure 6:
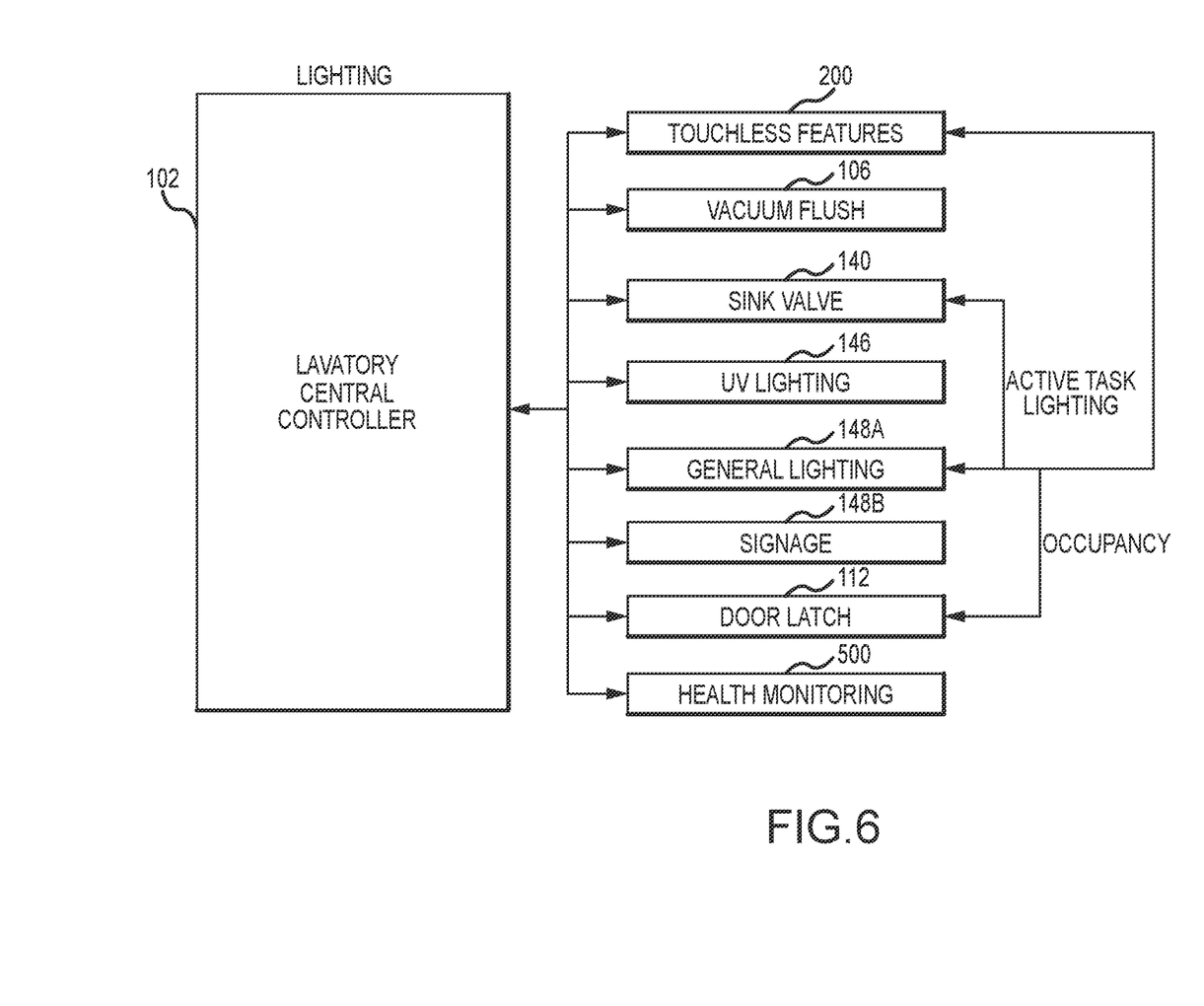

Referring now to FIGS. 4 and 6, an exemplary use of the method 400 for control of lighting within the lavatory is shown. In particular, the central controller may determine that a user has entered and locked the lavatory based on information received from the door latch sensor 112. In response to this determination, the central controller 102 may control general lighting of the lavatory to illuminate the lavatory, including a directed light source illuminating an area around a toilet. In response to the touchless flush sensor 206 receiving input to flush the toilet, the central controller 102 may control the directed light to cease illuminating the area around the toilet. Furthermore, in response to the sink valve 140 opening to supply water through the faucet, the central controller 102 may control the lighting to direct light towards the area of the faucet. The central controller 102 may then turn off all general lighting in response to the door latch 112 becoming unlocked.

Figure 7:
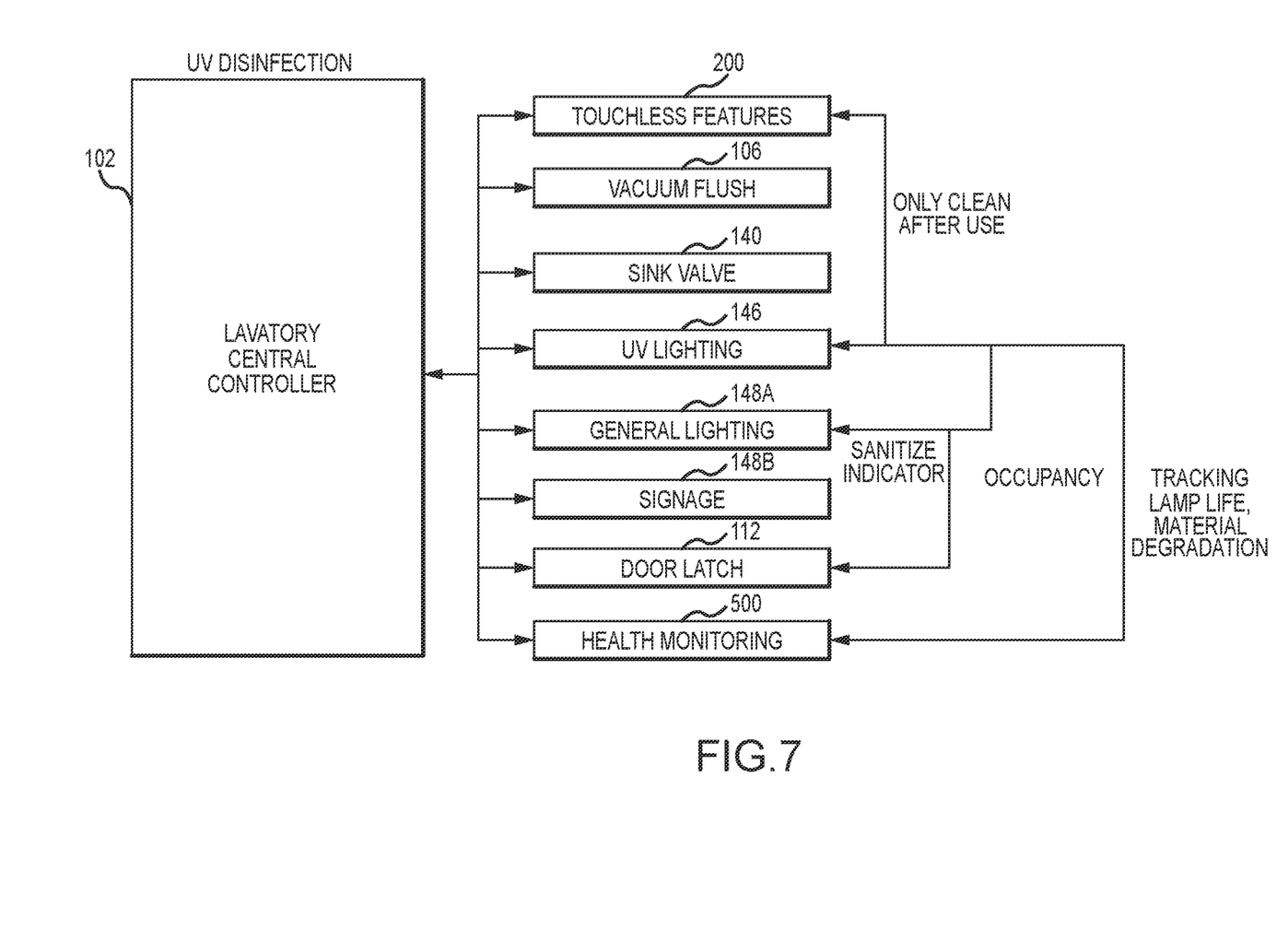

Referring to FIGS. 4 and 7, an exemplary use of the method 400 for control of UV disinfecting lighting to disinfect portions of the lavatory is shown. As discussed above, the UV light source 146 may include multiple UV light sources that each illuminate a specific area of the lavatory. For example, a toilet UV light source may illuminate the toilet, a door UV light source may illuminate a door handle, and a sink UV light source may illuminate the sink. Because it may be undesirable for the UV light to reach a human, it may be desirable to only emit the UV light in response to the lavatory being vacant. Additionally, it may be desirable to only illuminate portions of the lavatory using the UV light that were used in a prior use. In that regard, the central controller 102 may make inferences regarding which portions of the lavatory were used by the user. For example, the central controller may determine that the toilet was used in response to the touchless flush sensor 206 receiving a request to flush the toilet, may determine that the door handle was used in response to the door latch 112 being engaged, and may determine that the sink was used in response to the sink valve 140 turning on.

After the central controller 102 determines that the user has left the lavatory, the central controller 102 may control the UV light source 146 to illuminate the portions of the lavatory that were used by the user in order to disinfect those areas. In addition, the central controller 102 may control the visible light source 148B to indicate that disinfecting is occurring and to indicate that the lavatory should remain vacant.

Throughout the process, the health monitoring 500 may track a remaining life of each light source and may track a duration of exposure of each surface to the UV light. The central controller 102 may transmit a notification to an operator of the aircraft in response to the health monitoring 500 indicating that the remaining life (e.g., of a UV bulb) has reached or dropped below a threshold remaining life, or in response to the health monitoring 500 indicating that one or more surface of the lavatory has degraded to or beyond a threshold degradation level.

Figure 8:
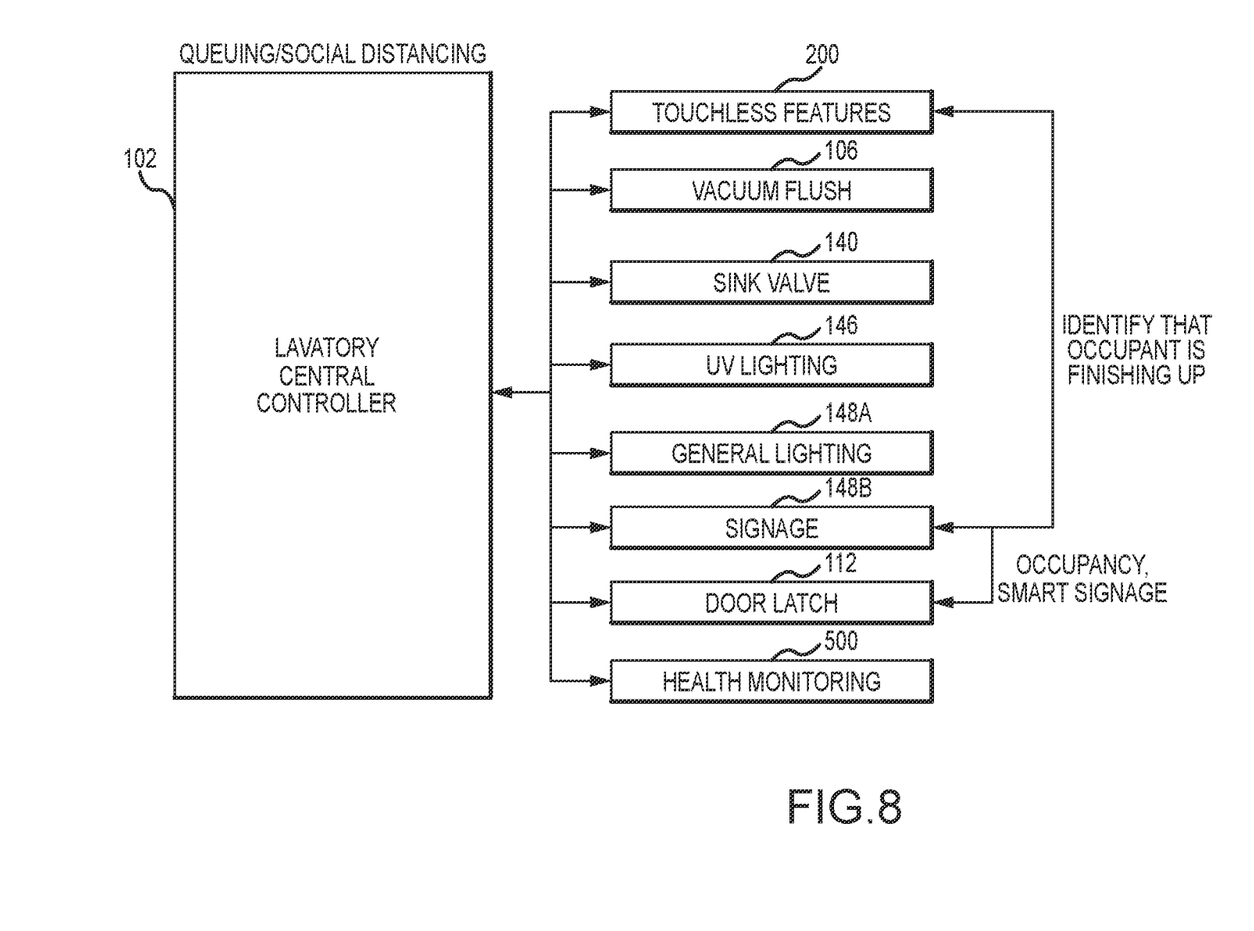

Referring to FIGS. 4 and 8, an exemplary use of the method 400 for controlling queuing and social distancing corresponding to lines or a waitlist to use the lavatory is shown. In response to the central controller 102 determining that the lavatory is occupied, the central controller 102 may control the visible light source 148B corresponding to signage to indicate that the lavatory is occupied. The central controller 102 may further determine that a user is finishing in the lavatory and may exit shortly in response to the touchless flush sensor 206 receiving a request to flush the toilet, or in response to the sink valve 140 turning on. In response to determining that the user is finishing in the lavatory, the central controller 102 may control a sign to indicate that the next passenger to use the lavatory may begin moving towards the lavatory. The central controller 102 may further monitor occupancy of multiple lavatories and may direct each waiting passenger to the lavatory that is most likely to be vacant next. The central controller 102 may further record a list of passengers waiting to use the lavatory (e.g., based on information received at a seat-back input device) and may notify each passenger when they are next, and may further notify the passenger of which lavatory to use.

Benefits and other advantages have been described herein with regard to specific embodiments. Furthermore, the connecting lines shown in the various figures contained herein are intended to represent exemplary functional relationships and/or physical couplings between the various elements. It should be noted that many alternative or additional functional relationships or physical connections may be present in a practical system. However, the benefits, advantages, and any elements that may cause any benefit or advantage to occur or become more pronounced are not to be construed as critical, required, or essential features or elements of the disclosure. The scope of the disclosure is accordingly to be limited by nothing other than the appended claims, in which reference to an element in the singular is not intended to mean "one and only one" unless explicitly so stated, but rather "one or more." Moreover, where a phrase similar to "at least one of A, B, or C" is used in the claims, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C.

Systems, methods and apparatus are provided herein. In the detailed description herein, references to "various embodiments", "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

Furthermore, no element, component, or method step in the present disclosure is intended to be dedicated to the public regardless of whether the element, component, or method step is explicitly recited in the claims. No claim element herein is to be construed under the provisions of 35 U.S.C. 12(f), unless the element is expressly recited using the phrase "means for." As used herein, the terms "comprises", "comprising", or any other variation thereof, are intended to cover a non-exclusive inclusion, such that a process, method, article, or apparatus that comprises a list of elements does not include only those elements but may include other elements not expressly listed or inherent to such process, method, article, or apparatus.

What is claimed is:

1. A system for touchless control of a lavatory of an aircraft, the system comprising:
    a plurality of touchless sensors located in the lavatory, wherein each of the plurality of touchless sensors is configured to receive data corresponding to the lavatory, wherein the plurality of touchless sensors comprises:
        a touchless seat sensor configured to receive a toilet seat request corresponding to a request to lift a toilet seat of the lavatory,
        a touchless lid sensor configured to receive a toilet lid request corresponding to a request to lift a toilet lid of the lavatory,
        a touchless soap sensor configured to receive a soap dispense request corresponding to a request to dispense soap within the lavatory,
        a touchless faucet sensor configured to detect a faucet request corresponding to a request to operate a faucet of the lavatory,
        a touchless flush sensor configured to detect a flush request corresponding to a request to flush a toilet of the lavatory; and
        a touchless trash sensor configured to detect a trash flap request corresponding to a request to actuate a trash flap of the lavatory;
    an actuator located in the lavatory and configured to perform a first action;
    a light source located in the lavatory and configured to perform a second action, wherein the light source includes an ultraviolet light source located in the lavatory configured to emit ultraviolet light having a wavelength that at least one of injures, neutralizes, or kills pathogens; and
    a central controller coupled to each of the plurality of touchless sensors, the actuator, and the light source, the central controller configured to:
        control the toilet seat of the lavatory in response to receiving the request to lift the toilet seat,
        control the toilet lid of the lavatory in response to receiving the request to lift the toilet lid,
        control dispensing of the soap from a soap dispenser in response to receiving the request to dispense the soap within the lavatory,
        control operation of the faucet in response to receiving the faucet request,
        control flushing of the toilet of the lavatory in response to receiving the flush request,
        control the trash flap in response to receiving the trash flap request,
        make an inference as to a portion of the lavatory that was used based on the data received from each of the plurality of touchless sensors,
        responsive to the inference, control at least one of the actuator and the light source to selectively illuminate the portion of the lavatory with one or more components, each of the one or more components associated with one or more of the plurality of touchless sensors from the inference, and
        determine a health status of the system, the health status including a remaining life of the ultraviolet light source, and to control the ultraviolet light source further based on the health status, wherein:
            the health status of the system further includes a surface wear experienced by one or more surfaces of the lavatory in response to the ultraviolet light,
            the surface wear of the health status is based at least in part on a duration for which the one or more surfaces was exposed to the ultraviolet light and a threshold duration of exposure of ultraviolet light associated with the one or more surfaces.

2. The system of claim 1, wherein the data received includes user input corresponding to requested operation of a component of the lavatory and the central controller is further configured to control the actuator or the light source based on the user input.

3. The system of claim 2, further comprising an actuator controller coupled to one of the actuator or the light source and connected to the central controller, wherein the central controller is configured to control the actuator or the light source by transmitting a control request to the actuator controller.

4. The system of claim 2, wherein the central controller is further coupled to the ultraviolet light source and configured to control the ultraviolet light source based on the data received.

5. The system of claim 4, wherein the light source further includes a visible light source located in the lavatory and configured to emit visible light having a visible wavelength, wherein the central controller is further configured to control the actuator or the light source to cause a total power draw of the system to remain at or below a power threshold corresponding to a maximum amount of power available to the system.

6. The system of claim 5, wherein the central controller is further configured to control the light source to at least partially operate sequentially to cause the total power draw of the system to remain at or below the power threshold.

7. The system of claim 4, wherein the health status of the system further includes a remaining quantity of supplies in the lavatory, and wherein the central controller further controls the actuator based on the health status.

8. The system of claim 1, wherein the inference includes at least one of an inferred portion of the lavatory used by a passenger for which sanitization is desirable or whether the lavatory is occupied.

9. A system for touchless control of a lavatory of an aircraft, the system comprising:
multiple sensors located in the lavatory and each of the multiple sensors is configured to receive data corresponding to the lavatory;
multiple actuators located in the lavatory and each configured to perform a first action, each of the multiple actuators associated with a respective sensor in the multiple sensors;
multiple light sources located in the lavatory and each configured to perform a second action, each of the multiple light sources comprising an ultraviolet light source located in the lavatory configured to emit ultraviolet light having a wavelength that at least one of injures, neutralizes, or kills pathogens; and
a central controller coupled to each of the multiple sensors, each of the multiple actuators, and each of the multiple light sources, the central controller configured to:
receive a request from each of the multiple sensors located in the lavatory;
responsive to receiving the request from a first of the multiple sensors, performing, via one of the multiple actuators associated with the first of the multiple sensors, the first action that corresponds to the first of the multiple sensors,
make an inference as to a portion of the lavatory that was used for which sanitization is desirable based on the data received from each of the multiple sensors, responsive to the inference, control at least one of the multiple actuators and the multiple light sources to selectively illuminate the portion of the lavatory with one or more components, each of the one or more components associated with one or more of the multiple sensors from the inference, and
determine a health status of the system, the health status including a remaining life of the multiple light sources, and to control the multiple light sources further based on the health status, wherein:
the health status of the system further includes a surface wear experienced by one or more surfaces of the lavatory in response to the ultraviolet light, the surface wear of the health status is based at least in part on a duration for which the one or more surfaces was exposed to the ultraviolet light and a threshold duration of exposure of ultraviolet light associated with the one or more surfaces.

10. The system of claim 9, wherein:
the multiple sensors include:
a touchless seat sensor configured to receive a toilet seat request corresponding to a request to lift a toilet seat of the lavatory,
a touchless lid sensor configured to receive a toilet lid request corresponding to a request to lift a toilet lid of the lavatory;
a touchless soap sensor configured to receive a soap dispense request corresponding to a request to dispense soap within the lavatory,
a touchless faucet sensor configured to detect a faucet request corresponding to a request to operate a faucet of the lavatory,
a touchless flush sensor configured to detect a flush request corresponding to a request to flush a toilet of the lavatory, and
a touchless trash sensor configured to detect a trash flap request corresponding to a request to actuate a trash flap of the lavatory;
the multiple actuators or light sources include:
a toilet seat actuator configured to actuate the toilet seat,
a soap actuator configured to dispense the soap,
a faucet actuator configured to actuate the faucet,
a trash flap actuator configured to actuate the trash flap,
a visible light source configured to emit visible light; and
the multiple light sources include:
multiple ultraviolet light sources configured to emit the ultraviolet light having the wavelength that at least one of injures, neutralizes, or kills pathogens.

11. The system of claim 10, wherein the central controller is further configured to control each of the multiple actuators and the multiple light sources to cause a total power draw of the system to remain at or below a power threshold corresponding to a maximum amount of power available to the system.

12. The system of claim 10, wherein the health status of the system further includes a remaining quantity of supplies in the lavatory, and wherein the central controller further controls at least one of the multiple actuators based on the health status.

13. The system of claim 9, wherein the inference includes whether the lavatory is occupied.

14. A method for touchless control of a lavatory of an aircraft, the method comprising:
receiving, by a central controller and from a first of a plurality of touchless sensors disposed in the lavatory, a request to perform an action,
control, by the central controller and via a first of a plurality of actuators, the action associated with the first of the plurality of touchless sensors receiving, by at least one sensor of the lavatory, data corresponding to the lavatory, the data including the request to perform the action;

making, by the central controller, an inference as to a portion of the lavatory that was used and for which sanitation is desirable based on the data received;

determining, by the central controller, a health status, the health status including a remaining life of at least one light source and a surface wear experienced by one or more surfaces of the lavatory in response to light emitted by the at least one light source, wherein the surface wear of the health status is based at least in part on a duration for which the one or more surfaces was exposed to ultraviolet light and a threshold duration of exposure of ultraviolet light associated with the one or more surfaces;

responsive to the inference, controlling, by the central controller, a first of at least one actuator or a first of the at least one light source of the lavatory to selectively illuminate the portion of the lavatory with one or more components, each of the one or more components associated with one or more of the at least one sensor from the inference; and responsive to the health status exceeding at threshold parameter, controlling, by the central controller, the first of the at least one actuator, a second of the at least one actuator, a first of the at least one light source, or a second of the at least one light source of the lavatory.

15. The method of claim 14, wherein the central controller is further configured to control the at least one actuator and the at least one light source to cause a total power draw of the lavatory to remain at or below a power threshold corresponding to a maximum amount of power available to the lavatory.

16. The method of claim 15, wherein the central controller is further configured to control the at least one actuator and the at least one light source to operate sequentially to cause the total power draw to remain at or below the power threshold.

17. The method of claim 14, wherein the health status further includes a remaining quantity of supplies in the lavatory.

18. The method of claim 14, wherein the inference includes whether the lavatory is occupied.

* * * * *